(12) United States Patent
Künzler et al.

(10) Patent No.: US 8,647,300 B2
(45) Date of Patent: Feb. 11, 2014

(54) DEVICE FOR CONNECTING A SUCTION HOSE

(75) Inventors: Hansruedi Künzler, Mettmenstetten (CH); Peter Vischer, Küssnacht am Rigi (CH); Urs Stadelmann, Lucerne (CH)

(73) Assignee: Medela Holding AG, Baar (CH)

( * ) Notice: Subject to any disclaimer, the term of this patent is extended or adjusted under 35 U.S.C. 154(b) by 333 days.

(21) Appl. No.: 12/739,000

(22) PCT Filed: Oct. 24, 2008

(86) PCT No.: PCT/CH2008/000447
§ 371 (c)(1),
(2), (4) Date: Apr. 21, 2010

(87) PCT Pub. No.: WO2009/055949
PCT Pub. Date: May 7, 2009

(65) Prior Publication Data
US 2010/0228188 A1    Sep. 9, 2010

(30) Foreign Application Priority Data

Oct. 30, 2007  (CH) ................................. 1680/07

(51) Int. Cl.
*A61M 5/00* (2006.01)
*A61M 1/06* (2006.01)
*A61M 25/16* (2006.01)

(52) U.S. Cl.
USPC .............................. 604/110; 604/74; 604/533

(58) Field of Classification Search
USPC ........................................... 604/74, 533–539
See application file for complete search history.

(56) References Cited

U.S. PATENT DOCUMENTS

| 3,876,234 A | 4/1975 | Harms |
| 4,123,091 A | 10/1978 | Cosentino et al. |

(Continued)

FOREIGN PATENT DOCUMENTS

| DE | 8804038 | 5/1988 |
| DE | 202005017522 | 1/2006 |

(Continued)

OTHER PUBLICATIONS

International Search Report for corresponding International Application No. PCT/CH2008/000447 dated Jan. 14, 2009.

(Continued)

*Primary Examiner* — Laura Bouchelle
*Assistant Examiner* — Jenna Zhang
(74) *Attorney, Agent, or Firm* — McDonnell Boehnen Hulbert & Berghoff LLP

(57) ABSTRACT

The device according to the invention for connecting a suction hose has a connecting piece which is designed in such a way that the suction hose can be pushed over a region of the connecting piece in a sealing manner. The device also comprises a sleeve which can be pushed over the aforementioned region of the connecting piece, at least partially covering said piece and leaving room between the sleeve and the connecting piece for the suction hose. The connection between the sleeve and the connecting piece can only be separated by the destruction of at least one of said two parts. The design of the exterior of the sleeve prevents a second suction hose from lying in a sealing manner against the sleeve. A suction hose that is connected in a sealing manner to the claimed device can therefore not be removed without destroying the device. In addition, it is impossible to push a hose with a greater diameter onto the sleeve in a sealing manner.

21 Claims, 6 Drawing Sheets

(56) References Cited

U.S. PATENT DOCUMENTS

| | | |
|---|---|---|
| 4,511,163 A | 4/1985 | Harris et al. |
| 4,607,868 A | 8/1986 | Harvey et al. |
| 4,749,217 A | 6/1988 | Causby et al. |
| 4,929,236 A * | 5/1990 | Sampson .................... 604/175 |
| 5,868,435 A | 2/1999 | Bartholomew |
| 5,988,700 A | 11/1999 | Prichard |
| 6,641,177 B1 * | 11/2003 | Pinciaro ..................... 285/242 |
| 6,699,213 B1 * | 3/2004 | Annis et al. ................. 604/74 |
| 2003/0001385 A1 | 1/2003 | Favre et al. |
| 2005/0043677 A1 | 2/2005 | Kelly et al. |
| 2005/0085794 A1 | 4/2005 | Denoth et al. |

FOREIGN PATENT DOCUMENTS

| | | |
|---|---|---|
| EP | 1468705 | 10/2004 |
| EP | 1552858 | 7/2005 |
| EP | 1821021 | 8/2007 |
| EP | 1902747 | 3/2008 |
| WO | 98/24500 | 6/1998 |
| WO | 2006/004943 | 1/2006 |

OTHER PUBLICATIONS

International Preliminary Report on Patentability and Written Opinion for corresponding PCT Application No. PCT/CH2008/000447, dated Jul. 8, 2010.

Swiss Search Report for corresponding Swiss Patent Application No. 1680/07, dated Jun. 11, 2008.

\* cited by examiner

DEVICE FOR CONNECTING A SUCTION HOSE

CROSS REFERENCE TO RELATED APPLICATIONS

This application claims priority to International Application Serial No. PCT/CH2008/000447 filed Oct. 24, 2008, which claims priority to Swiss Patent Application No. 01680/07 filed Oct. 30, 2007, the contents of which are incorporated by reference herein in their entirety.

TECHNICAL FIELD

The invention relates to a device for connecting a suction tube.

PRIOR ART

Tube connections of very different kinds are known in large number in the prior art, in particular for suction tubes and drainage tubes in the medical field. Examples are described in EP 1 552 858, U.S. Pat. No. 3,876,234, U.S. Pat. No. 4,123,091, U.S. Pat. No. 4,511,163, U.S. Pat. No. 4,607,868, U.S. Pat. No. 5,988,700 and WO 98/24500.

In a tube connection, or device for connecting a tube, the tube is usually pushed onto or into a connector piece and fixed by virtue of the shape of the connector piece or by means of an additional securing part.

In most devices, the suction tubes can be easily replaced. However, there are areas of use, for example in drainage applications, such as chest drainage, or in breastpumps for pumping off human breastmilk, where it is not desirable for the suction tube to be able to be removed from the device and possibly replaced by another one. Some reasons for this are hygiene, functional safety of the pump system, and protection against cheap or unsatisfactory copies of replacement parts.

DISCLOSURE OF THE INVENTION

It is therefore an object of the invention to make available a device for connecting a suction tube, which device prevents the suction tube from being removed without destruction and prevents the suction tube from being replaced by another tube.

The device according to the invention for connecting a suction tube has a connector piece which is designed in such a way that the suction tube can be pushed sealingly over an area of the connector piece. The device further comprises a sleeve which can be pushed over an area of the connector piece and at least partially covers the latter, leaving room for the suction tube between sleeve and connector piece. The connection between sleeve and connector piece can be separated only by destroying at least one of the two parts, preferably both parts. The sleeve has an outer surface configuration that prevents a second suction tube from bearing sealingly on the sleeve.

In this way, a tube that has been connected sealingly at the time of manufacture or in the factory cannot be removed without destruction and refitted. The device and tube are prevented from being connected to each other improperly. The functional reliability of the device and its compliance with hygiene requirements are ensured. It is also ensured that no cheap tube can be used instead of the original tube.

Moreover, a tube that has been fitted at the time of manufacture cannot simply be cut off and replaced by a replacement tube of greater diameter that is pushed over the sleeve. The outer shape of the sleeve makes it impossible to obtain a sealed connection with such a replacement tube. This also ensures the functional safety of the suction unit, since another suction diameter would cause another suction action.

This also ensures that all the parts of the device that are connected to one another at the time of manufacture can be used only for the length of time envisioned by the manufacturer or until any one of the parts becomes contaminated or suffers a defect.

It also prevents easy-to-produce, unsatisfactory and cheap copies of individual parts of the device from being offered for sale. This is especially important in drainage and in breastpumps, since in these cases the breastshields, tubes and other parts of a suction unit used on the patient or mother, respectively, are disposable articles and are used in large numbers, but must nonetheless meet strict quality criteria.

In a preferred embodiment, the sleeve has a main body with an external diameter and has an outer flange which is formed integrally on the main body and which has a diameter greater than said external diameter, wherein the flange is at least partial circumferential and has a contour deviating from a circle shape.

The connector piece and sleeve are preferably made of plastic, particularly by injection molding. In this way, these parts can be produced inexpensively.

The connector piece and sleeve are preferably connected to each other by a snap-fit closure, such that the parts have a relatively simple shape and can therefore be inexpensively produced, particularly by injection molding.

The sleeve preferably contributes to sealing or fixing the suction tube. However, the sleeve can also rest on the latter in a manner free from pressure or can even be spaced apart from it.

The sleeve has the further advantage that it protects the tube from outside in the connection area thereof. If, moreover, the sleeve protrudes beyond the connector piece, it protects the suction tube from kinking and possibly breaking in this area.

Further advantageous embodiments are set forth in the dependent claims.

BRIEF DESCRIPTION OF THE DRAWINGS

The subject matter of the invention is explained below on the basis of a preferred illustrative embodiment depicted in the attached drawings, in which:

FIG. 4b shows a variant of the detail according to FIG. 4a;

DETAILED DESCRIPTION

The illustrative embodiment described below relates to a device for sealingly connecting a suction tube to a diaphragm cap of a breastpump for pumping off human breastmilk. A diaphragm cap of this kind is known from U.S. Pat. No. 6,699,213.

The inventive teaching, however, is not limited to this type of use. For example, the device according to the invention can be used, in the technical field of breastpumps, also for differently configured diaphragm caps, for connections to the pump itself, and for connection to the breastshield. Moreover, it can be used analogously in the field of drainage, particularly in wound drainage or chest drainage, or in other fields, particularly in medical technology.

Figure 1:
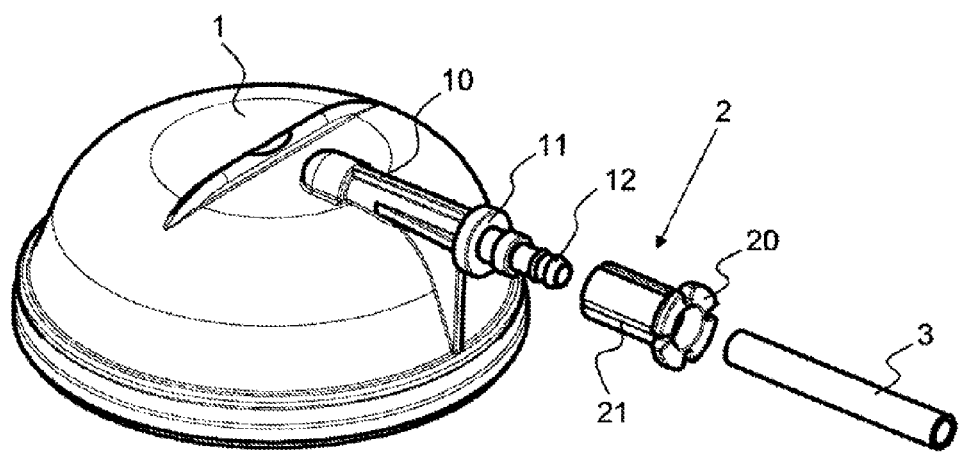
FIG. 1 is a perspective view of a diaphragm cap of a breastpump, with a device according to the invention for connecting a suction tube shown in an exploded view.
Figure 2:
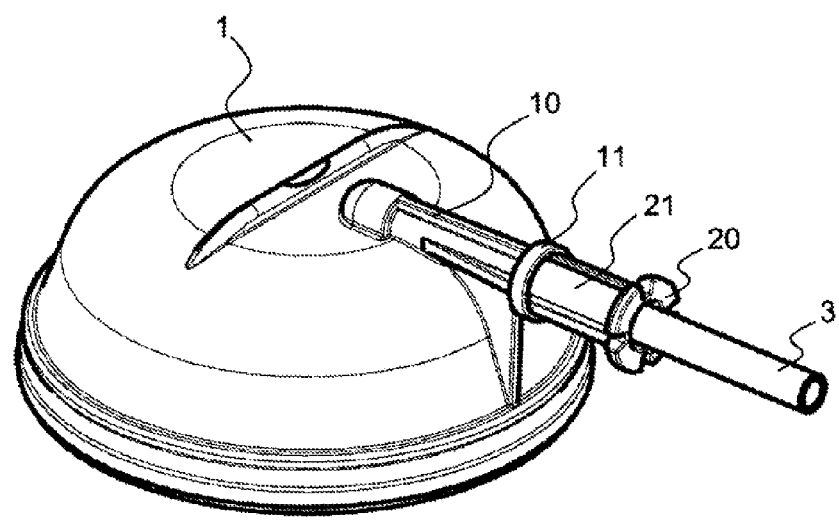
FIG. 2 shows the diaphragm cap with the device according to FIG. 1 in the assembled state.
Figure 3A:
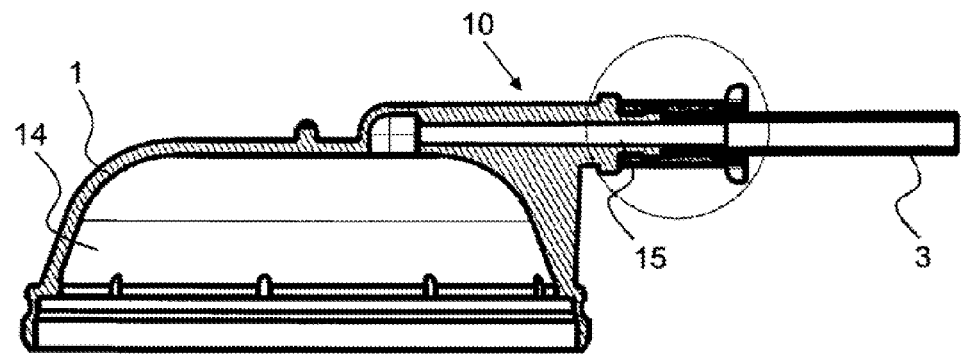
FIG. 3a shows a longitudinal section through the cap with the device according to FIG. 1.

The diaphragm cap 1 shown in FIGS. 1 to 3 has a usually stiff, bowl-shaped hood with an inner cavity 14. It is fitted onto a pump diaphragm of a suction pump and connected tightly thereto. The cavity 14 communicates with the outside by way of a conduit 15 that runs inside a connector piece 10. The connector piece 10 is connected fixedly to the diaphragm cap 1. The connector piece 10 is in this case produced in one piece with the latter in a plastic injection molding operation. The connector piece 10 is preferably of inherently rigid design.

The free end 12 of the connector piece 10 protruding from the diaphragm cap 1 serves to receive a first end of a suction tube 3, which is shown only as a small portion in the figures. The suction tube 3 is turned or pushed over this free end 12.

A sleeve 2 is pushed over the suction tube 3 and the free end 12 of the connector piece 10 and bears with its end directed away from the tube against an outer flange 11 protruding outward from the connector piece 10. This can be seen in FIG. 2. The sleeve 2 preferably has a hollow cylindrical main body 21, and a radially outwardly protruding protective ring or flange 20 formed integrally thereon at the end directed away from the connector piece. The sleeve 2 is also preferably produced in a plastic injection molding operation.

The suction tube 3 is connected at its second end to a breastshield (not shown here), which is used for placing on a human breast. The connection of the suction tube to the breastshield can be releasable or fixed. In the latter case, separation is not possible without destruction.

Figure 4A:
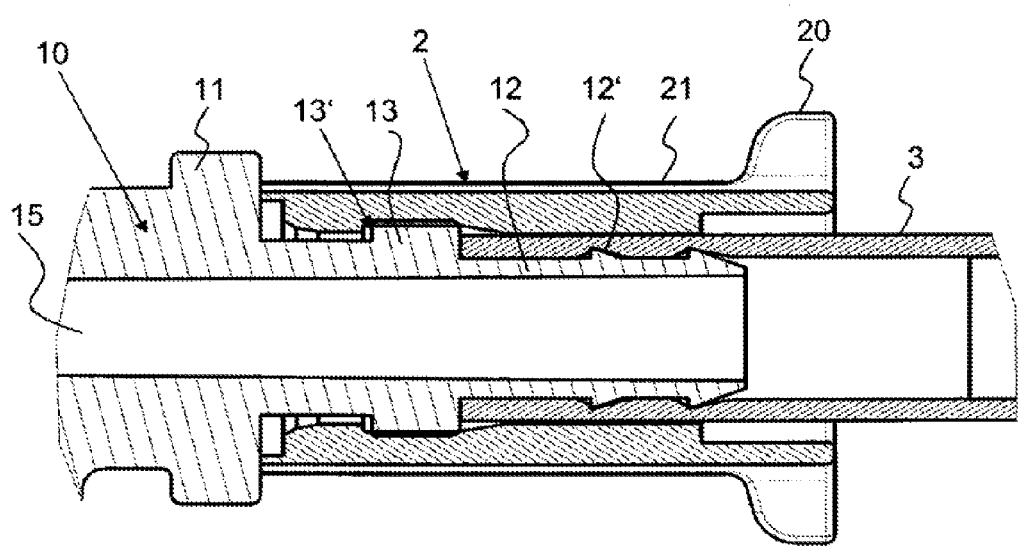
FIG. 4a shows an enlarged view of a detail from FIG. 3.
Figure 4B:
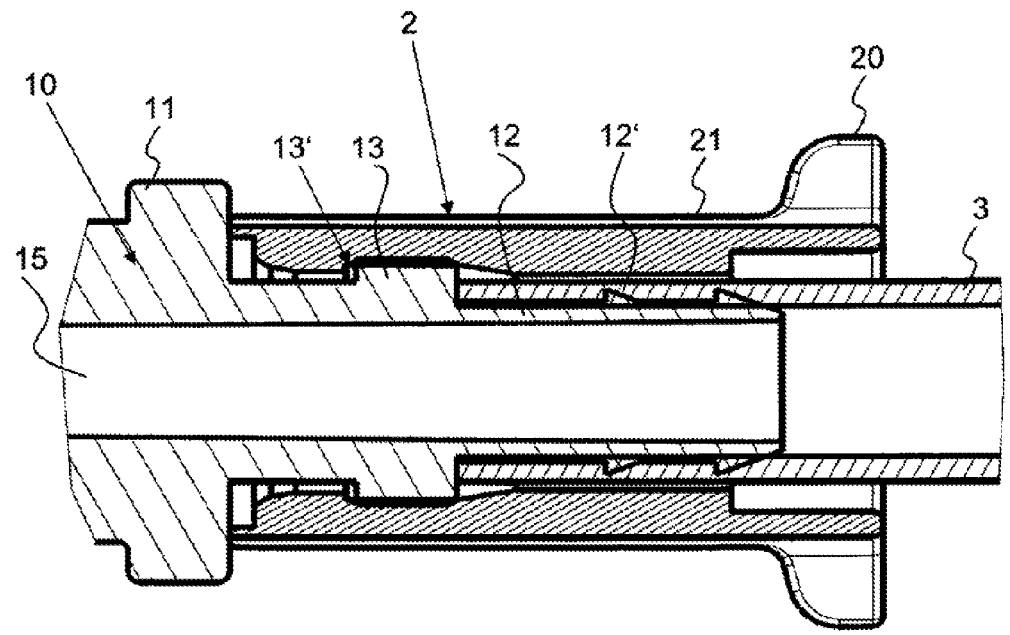
Figure 5:
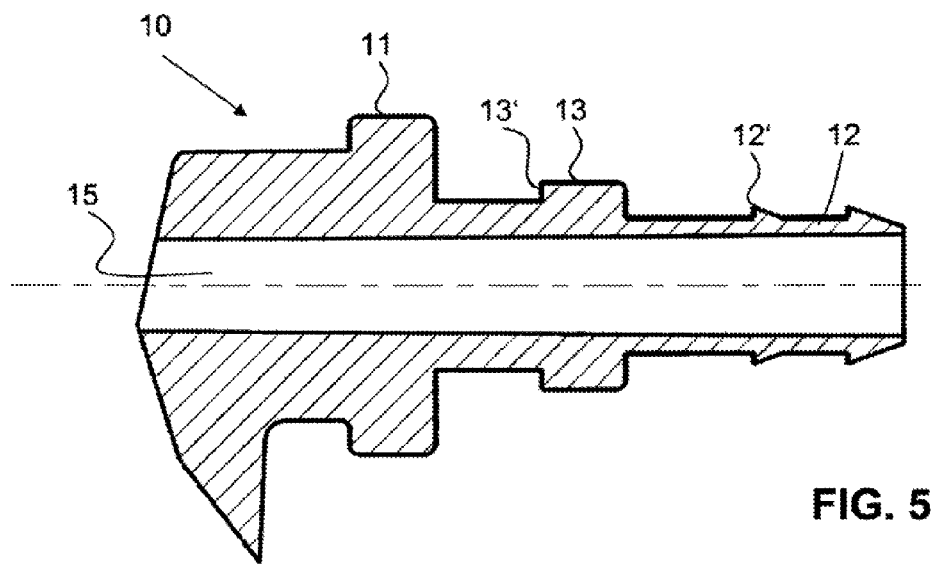
FIG. 5 shows an enlarged view of a connector piece according to the invention in longitudinal section.
Figure 6:
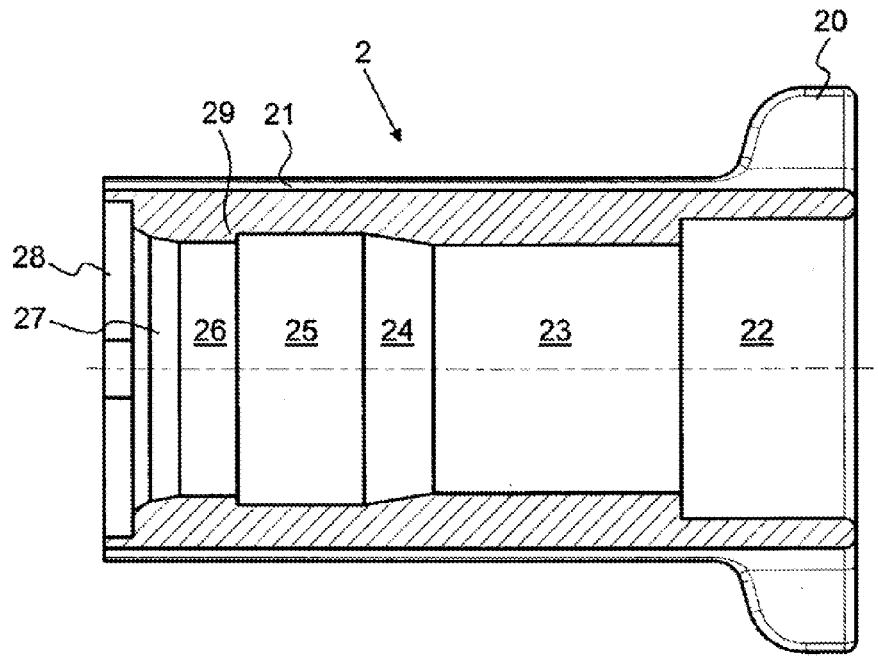
FIG. 6 shows a longitudinal section through a sleeve according to the invention.

In FIGS. 4 to 6, the connector piece 10, the sleeve 2, and the snap-fit connection of these two parts, are shown in detail. As is shown in FIG. 5, the connector piece 10 has an outer contour comprising abrupt changes in the longitudinal direction. An inner contour of the sleeve 2 changes correspondingly abruptly in its longitudinal direction, as is shown in FIG. 6. In this way, a connection between connector piece 10 and sleeve 2 can be created that is releasable only with destruction. A connection of this kind can also be obtained by a different shape of the two parts. However, the connection is preferably a force-fit and/or form-fit connection.

At its free end 12 directed toward the tube, the connector piece according to FIG. 5 is provided with sealing ribs 12' which, preferably on the end facing away from the tube, are designed with a sharp edge or an incline, particularly a steep incline. The tube 3 can be pushed over the free end 12 and is held sealingly and fixedly by virtue of the ribs 12', as is shown in FIG. 4. The tube 3 can in this case be pushed on as far as a radially outwardly protruding inner flange 13 of the connector piece 10. This inner flange 13 has a smaller diameter than the outer flange 11. It forms a sharp and/or right-angled edge 13' at least in the direction toward the outer flange 11, that is to say on its side facing away from the tube.

The sleeve according to FIG. 6 has an inner contour with several areas, in this case seven areas 22-28, which merge into one another by steps and some of which have different internal diameters. A circumferential step or abutment edge 29 between two areas, here between the fourth area 25 and the fifth area 26, likewise has a right-angled and/or sharp-edged design. The areas 25, 26 here merge from a smaller internal diameter to a greater internal diameter in the direction toward the tube end.

The sleeve 2 can now be pushed initially over the tube 3 and, after the tube 3 has been pushed over the connector piece 10, the sleeve 2 can likewise be pressed or pushed over this. The sleeve 2 slides with its step 29 over the inner flange 13 until its end face directed away from the tube bears on the outer flange 11. It is now no longer possible to pull the sleeve 2 back, since its edge 29 bears on the edge 13' of the connector piece 10. The connection can therefore be released only by destroying the sleeve 2 and/or connector piece 10.

As can be seen from FIG. 4a, the sleeve 2 serves as a fixing or sealing means in respect of the tube 3. It thus lies with pressure on the tube 3.

However, as can be seen in FIG. 4b, it is also possible that the sleeve 2 does not serve as a fixing or sealing means in respect of the tube 3. In this case, for example, it either lies on the tube 3 in a manner as far as possible free of pressure or, as shown here, it leaves a space free between itself and the tube along the whole of their joint length.

The sleeve 2 also serves as a means of protection from the outside and if, as is shown here, its end near the tube protrudes beyond the connector piece 10, it protects the tube 3 from kinking It thus increases the stiffness of the tube connection.

Figure 3B:
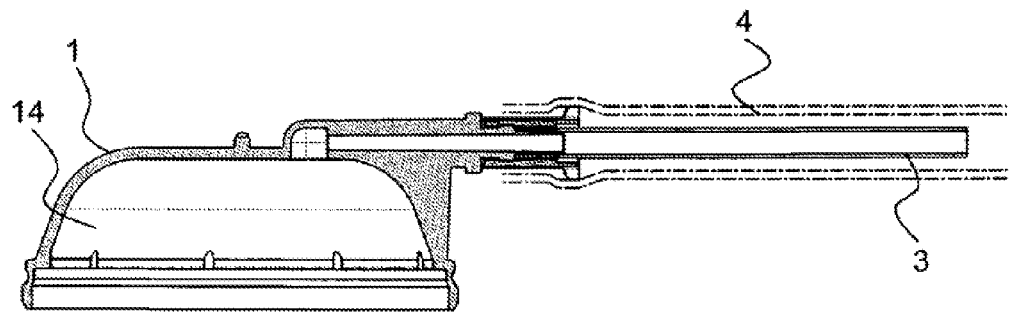
FIG. 3b shows the longitudinal section according to FIG. 3a with an incorrect replacement tube fitted.

According to the invention, the sleeve 2 now has an outer surface configuration that prevents a second suction tube 4 from bearing sealingly on the sleeve 2, as can be seen from FIG. 3b. This is preferably achieved by the fact that the outer contour of the sleeve 2, at least over a partial area, has a shape deviating from a circle shape.

Figure 7:
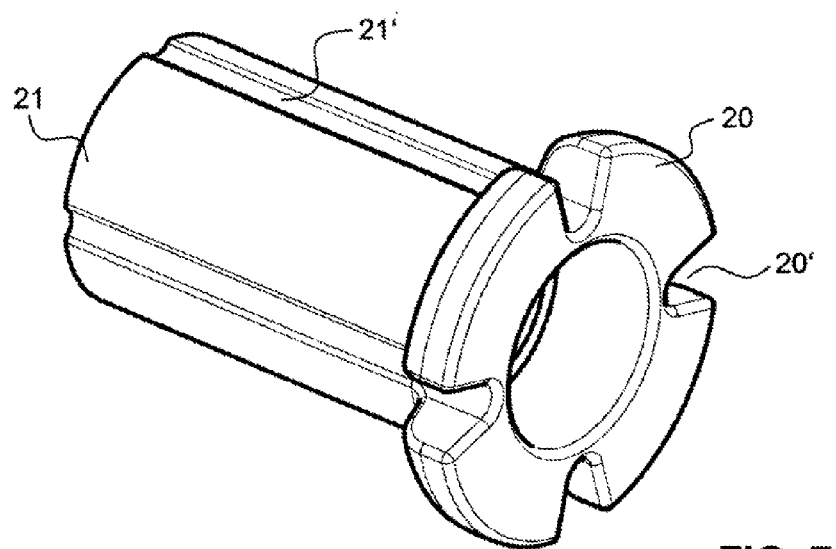
FIG. 7 shows a perspective view of the sleeve according to FIG. 6 from a first side.
Figure 8:
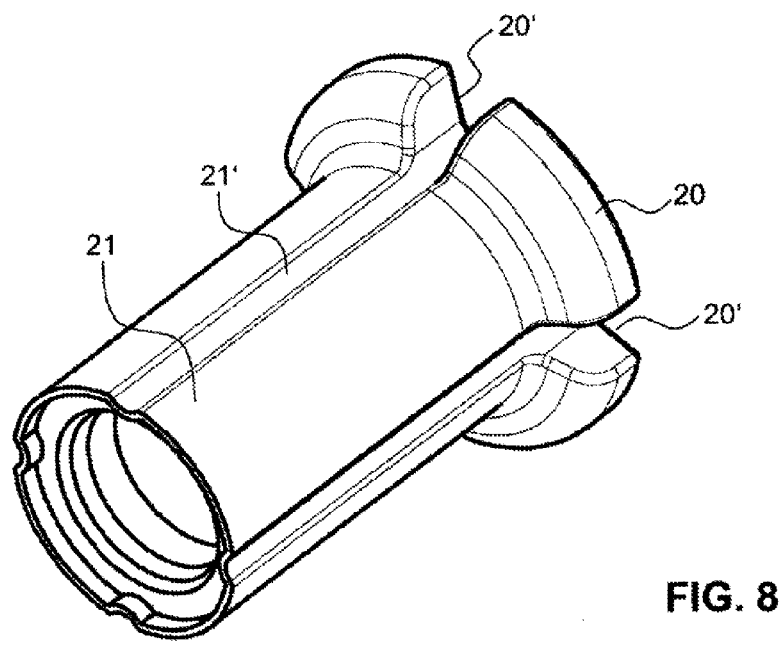
FIG. 8 shows a perspective view of the sleeve according to FIG. 6 from a second side.

For this purpose, in the example shown here according to FIGS. 7 and 8, the sleeve 2 has a flange 20, which is at least partially circumferential, but here extends around the full circumference, and which has a rosette-shaped design with recesses or indents 20' distributed about its periphery. Its flank directed away from the tube is preferably rounded or shaped with a gentle incline. The flange 20 is preferably arranged on that end of the sleeve which is directed away from the connector piece. However, it can also be located at the end near the connector piece or in an area therebetween.

In addition, ribs and/or grooves 21' are preferably present in the main body 21 of the sleeve 2. They preferably adjoin the depressions or indents 20' of the flange 20 and extend parallel to the longitudinal axis of the main body 21. Instead of or in addition to the ribs or grooves 21', knobs or dimples or other types of depressions and/or elevations may be present. In the example shown here, axially parallel grooves 21' are present that adjoin the depressions 20'.

The device according to the invention can now preferably be used in a connection unit of a breastpump for pumping off human breastmilk, wherein the unit comprises this device and the suction tube, which can be connected to a breastshield. This connection to the breastshield can be releasable again or can be releasable only with destruction. In the second case, the breastshield forms a suction unit together with said connection unit. Moreover, a breastmilk bottle attached to the breastshield, or another milk-collecting receptacle, can also be a component part of the suction unit.

Figure 9:
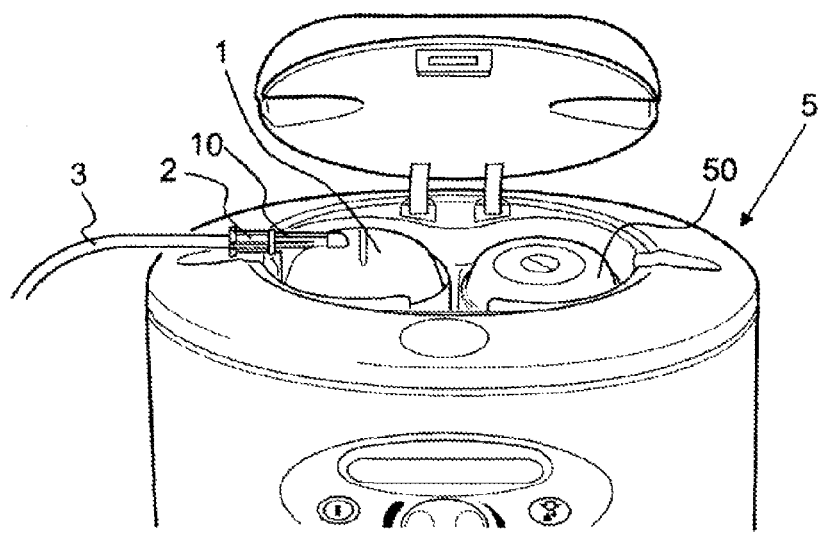
FIG. 9 shows a part of a breastpump with diaphragm cap and device according to the invention.

Alternatively or in addition to this, the connection unit can be connected at the breastpump end to a diaphragm cap. FIG. 9 shows an upper part of a breastpump 5 with two pump diaphragms 50 arranged next to each other. One of them is covered by a diaphragm cap 1, to which a suction tube 3 is secured.

If, as is shown here, the connection between diaphragm cap and connection unit can be separated only with destruction, the diaphragm cap is once again a component part of the connection unit.

Figure 10:
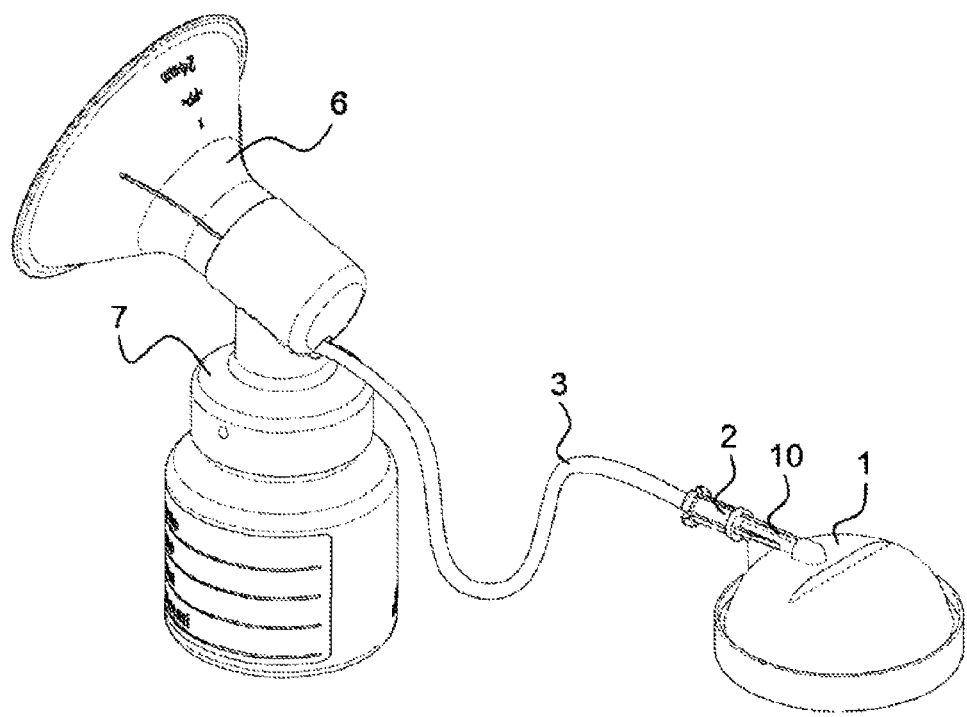
FIG. 10 shows a perspective view of a replacement kit with diaphragm cap, device according to the invention, breastshield, and breastmilk bottle.

A preferred combination of these elements leads to a replacement kit, or suction unit for breastpumps, that comprises at least one device according to the invention, a diaphragm cap 1 connected to the connector piece 10 integrally or only with destruction, a suction tube 3 pushed onto the connector piece 10 and covered by the sleeve 2, and a breastshield 6 connected to the other end of the suction tube 3 releasably or in a manner releasable only with destruction. The breastshield 6 can additionally be screwed onto a breastmilk bottle 7 or onto a milk-collecting receptacle. A corresponding example is shown in FIG. 10.

Thus, a suction tube connected sealingly to this device according to the invention cannot be removed from the device without being destroyed. Moreover, no tube with a greater diameter can be pushed sealingly onto the sleeve.

The invention claimed is:

1. A device for connecting a suction tube, wherein the device has a connector piece which is designed in such a way that the suction tube can be pushed sealingly over an area of the connector piece, wherein the device further comprises a sleeve which can be pushed over said area of the connector piece and at least partially covers said area of the connector piece, leaving room for the suction tube between the sleeve and the connector piece, wherein the sleeve has a main body with an external diameter and has an outer flange formed integrally on the main body, the outer flange having a diameter greater than said external diameter when the sleeve is pushed over the connector piece, such that the outer flange has an outer surface configuration that prevents a second suction tube from bearing sealingly on the sleeve, and wherein the sleeve has a continuous inner circumference including a circumferential abutment edge, and the connector piece has a radially outwardly protruding first flange which bears against the circumferential abutment edge in the direction counter to a direction of pushing-on of the sleeve, the circumferential abutment edge and the radially outwardly protruding first flange both having a right-angled and/or sharp-edged design, such that the connection between the sleeve and the connector piece can be separated only by destroying at least one of the sleeve and the connector piece.

2. The device as claimed in claim 1, wherein the connection between the sleeve and the connector piece can be separated only by destroying both the sleeve and the connector piece.

3. The device as claimed in claim 1, wherein the outer flange of the sleeve is at least partially circumferential and has an outer contour deviating from a circle shape.

4. The device as claimed in claim 3, wherein the outer flange of the sleeve has a rosette shaped design.

5. The device as claimed in claim 3, wherein the outer flange of the sleeve has depressions, which are adjoined by depressions of the main body.

6. The device as claimed in claim 3, wherein the outer flange of the sleeve is arranged on an end of the sleeve directed away from the connector piece.

7. The device as claimed in claim 1, wherein the sleeve can be connected to the connector piece with a form fit or force fit.

8. The device as claimed in claim 1, wherein the sleeve can be connected to the connector piece by a snap-fit closure.

9. The device as claimed in claim 8, wherein the sleeve has an inner contour comprising abrupt changes in the longitudinal direction of the sleeve, wherein the connector piece has an outer contour comprising abrupt changes in the longitudinal direction of the connector piece corresponding to the changes in said inner contour, and wherein the snap-fit closure is formed by means of the inner contour and the outer contour.

10. The device as claimed in claim 1, wherein the sleeve has a through-opening with an internal diameter that changes several times along its length.

11. The device as claimed in claim 1, wherein the connector piece has a free end with sealing ribs for sealingly receiving the suction tube.

12. The device as claimed in claim 1, wherein the sleeve has a substantially hollow cylindrical shape and has depressions and/or elevations on its outer surface.

13. The device as claimed in claim 12, wherein the depressions and/or elevations are arranged parallel to a longitudinal axis of the sleeve.

14. The device as claimed in claim 1, wherein the sleeve and the connector piece are made of plastic.

15. The device as claimed in claim 1, wherein the connector piece has a radially outwardly protruding second flange which serves as an abutment for the sleeve.

16. A connection unit of a breastpump for pumping off human breastmilk comprising:
   a suction tube having a first end and a second end, the first end being connected to the breastpump;
   a sleeve connected to the second end of the suction tube, the sleeve having a main body with an external diameter and having an outer flange formed integrally on the main body, the outer flange having a diameter greater than the external diameter when the sleeve is pushed over the connector piece, such that the outer flange prevents a second suction tube from being attached to the sleeve and the sleeve having a continuous inner circumference; and
   a connector piece connected to the sleeve;
   wherein the continuous inner circumference of the sleeve has a circumferential abutment edge, and the connector piece has a radially outwardly protruding flange which bears against the circumferential abutment edge in the direction counter to a direction of pushing-on of the sleeve, the circumferential abutment edge and the radially outwardly protruding flange both having a right-angled and/or sharp-edged design, such that the connection between the sleeve and the connector piece can be separated only by destroying-at least one of the sleeve and the connector piece.

17. The connection unit as claimed in claim 16, wherein the device can be connected at the breastpump end to a diaphragm cap that protects a pump diaphragm and that can be removed from the pump diaphragm.

18. The connection unit as claimed in claim 17, wherein the connector piece is connected to the diaphragm cap such that it can be removed only by destroying the diaphragm.

19. The connection unit as claimed in claim 18, wherein the connector piece is formed integrally on the diaphragm cap.

20. The connection unit as claimed in claim 17, wherein the diaphragm cap is made of plastic.

21. The connection unit of claim 16 further comprising a breastshield located on the breastpump for placing on a breast, wherein the suction tube is connected at a second end to the breastshield.

\* \* \* \* \*